United States Patent [19]

Deeg et al.

[11] 4,015,965
[45] Apr. 5, 1977

[54] METHOD OF MAKING ARTIFICIAL INTRAOCULAR LENSES WITH HOLES

[75] Inventors: Emil W. Deeg, Woodstock, Conn.; David A. Krohn, Southbridge, Mass.

[73] Assignee: American Optical Corporation, Southbridge, Mass.

[22] Filed: Dec. 22, 1975

[21] Appl. No.: 642,927

[52] U.S. Cl. .................................. 65/23; 65/31; 65/61; 65/DIG. 7
[51] Int. Cl.² .................. C03C 19/08; C03C 15/00
[58] Field of Search .......................... 65/23, 61, 31

[56] References Cited
UNITED STATES PATENTS

| 988,424 | 4/1911 | Woegerer | 65/23 |
|---|---|---|---|
| 2,156,156 | 4/1939 | Mallck | 65/23 X |
| 2,619,438 | 11/1952 | Varian et al. | 65/61 X |
| 2,752,731 | 7/1956 | Altosaar | 65/23 |
| 2,825,184 | 3/1958 | Charlotte | 65/61 X |
| 3,244,776 | 4/1966 | Sheldon | 65/61 X |
| 3,770,405 | 11/1973 | DeAngelis et al. | 65/23 |
| 3,925,825 | 12/1975 | Richards et al. | 3/13 |

Primary Examiner—S. Leon Bashore
Assistant Examiner—Frank W. Miga
Attorney, Agent, or Firm—H. R. Berkenstock, Jr.; William C. Nealon

[57] ABSTRACT

Making perforate optical sections (lenses) of pseudophakoi with avoidance of drilling operations and adversities thereof. Lens material is cast over wires corresponding in diametral size and relative juxtaposition to the size and spaced locations of holes needed in a lens and the wires are etched away prior to or following final edging and surface finishing of the lens. The casting of multiple lens preforms is contemplated.

8 Claims, 17 Drawing Figures

U.S. Patent  April 5, 1977  Sheet 1 of 2  4,015,965
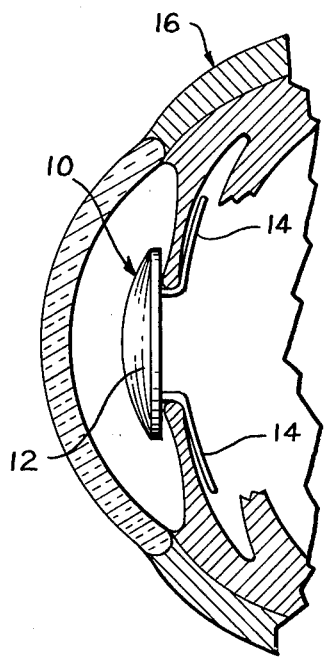
Fig. 1
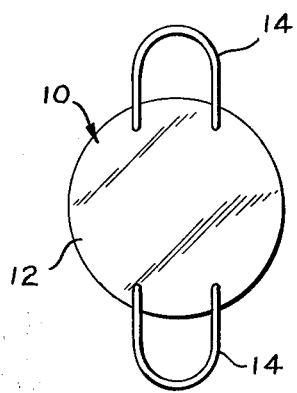
Fig. 2
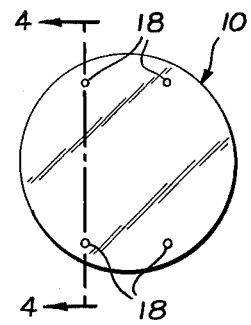
Fig. 3
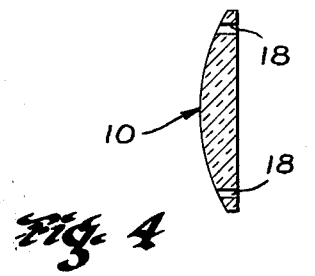
Fig. 4
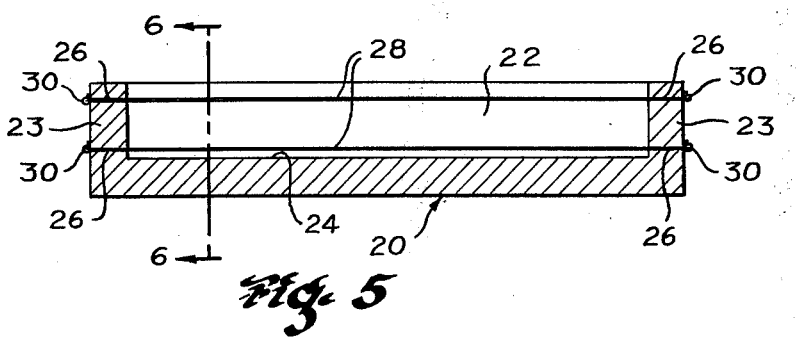
Fig. 5
Fig. 6
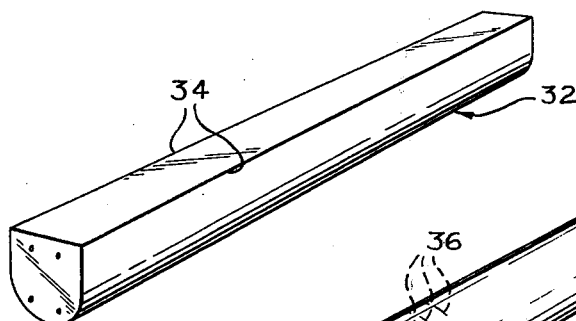
Fig. 7
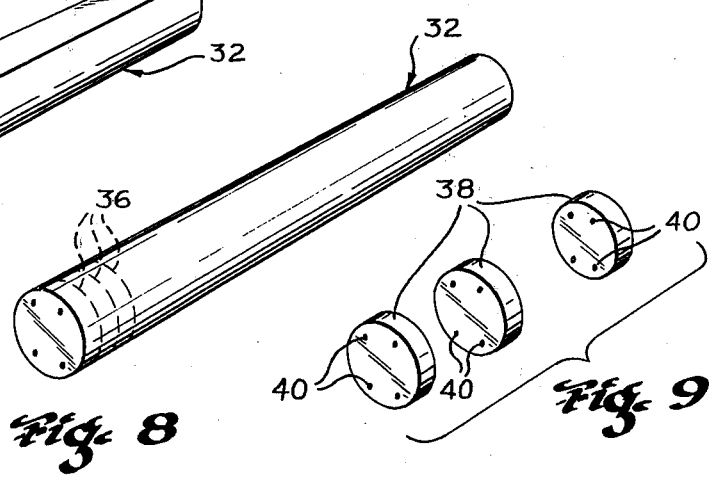
Fig. 8
Fig. 9

METHOD OF MAKING ARTIFICIAL INTRAOCULAR LENSES WITH HOLES

BACKGROUND OF THE INVENTION

1. Field of the Invention

This invention relates to improvements in method of manufacturing artificial intraocular lenses (pseudophakoi) and has particular reference to the manufacture of perforate optical sections (lenses) of pseudophakoi to which haptic sections (iris clips) may be fitted.

2. Discussion of the Prior Art

Well-fixed and well-centered intraocular lens implants are known to produce stable retinal images and offer the best chance of re-establishment of binocularity in cases of aphakia.

Many techniques of lens implantation, including suturing to the ciliary muscle as disclosed in U.S. Pat. No. 3,711,870 and iris diaphragm fixation as discussed in U.S. Pat. No. 3,673,616 for example, have been used. The latter is considered to be a safe procedure giving good stability and the present invention deals more particularly with improvements in this general type of pseudophakos but also has applicability to the former and/or any other type of pseudophakos requiring the provision of holes in its lens through which sutures may be extended or within which iris clips or other fastening wires may be inserted and anchored.

In cases of iris diaphragm fixation, "iridocapsular" and/or "iris clip" pseudophakoi are used. These implants are provided with a fastening section comprised of posterior and/or anterior iris clips usually in the form of loops or struts of wire or wirelike material, the ends of which are anchored in holes provided in the lens of the pseudophakos.

In view of a requirement for carefully controlled exceptionally close tolerances of hole size and the minuteness required of such holes, e.g. from 0.1 to 0.2 mm for lenses having a full diameter of only approximately 4 mm, the practice heretofore of forming such holes with drills has presented serious problems of tediousness, high scrap yield and excessive product cost, not to mention other adversities such as roughness or incipient cracking of lens material within the holes and/or chipping or flaking adjacent or at opposite ends of the holes, all of which tend to weaken the lens structure and render it subject to damage when wire iris clips and the like are anchored by interference fitting as is customary.

A principal object of the present invention is to provide pseudophakoi of improved construction and more particularly to provide a novel method for manufacturing perforate optical sections (lenses) of pseudophakoi in a manner which overcomes the aforementioned and related disadvantages of prior art techniques. Another object of the invention to provide for the manufacture of perforate artificial intraocular lenses in an unusually simple, rapid and economical manner wherewith manufacturing output can be readily maximized at minimum product cost with improved end product quality and dependability of duplication in mass production.

SUMMARY OF THE INVENTION

The aforesaid objectives and their corollaries are accomplished by casting a lens-forming material over wires corresponding in diametral size and relative juxtaposition to the size and spaced location of holes needed in a lens. The casting of multiple lens preforms is contemplated from which individual lenses may be subsequently separated. In either the case of casting lenses individually or in multiple lens preforms from which the individual lenses may be cut, wires therewithin are removed, i.e. etched away, at a stage of the process either preceding or following final edge and surface finishing. This removal of the wires, accordingly, leaves openings in their place which have walls of a surface texture substantially corresponding to the outer surface finish of wires used to form the same. Thus, the walls may be rendered free of incipient cracking, chipping, flaking or other roughness not uncommon to holes produced by prior art drilling operations.

Details of the invention will become more readily apparent from the following description when taken in conjunction with the accompanying drawings.

IN THE DRAWINGS

FIG. 1 is an illustration, in partial cross-section, of an exemplary pseudophakos in situ;

FIG. 2 is a rear elevational view of the pseudophakos of FIG. 1;

FIG. 3 is a rear elevational view of the ophthalmic section (lens) of the pseudophakos illustrating an exemplary number and position of holes which are provided therein for receiving and anchoring the haptic section (iris clips) of the pseudophakos;

FIG. 4 is a cross-sectional view taken generally along line 4—4 of FIG. 3;

FIG. 5 is a longitudinal cross-sectional view of one form of a mold which may be used to cast preforms of artificial intraocular lenses according to the invention;

FIG. 6 is a view taken generally along line 6—6 of FIG. 5;

FIG. 7 is an illustration, in perspective, of a preform of lens material of the type producable with a mold such as that shown in FIGS. 5 and 6.

FIG. 8 is an illustration, in perspective, of the results of a shaping operation which may be performed upon preforms such as that shown in FIG. 7 for facilitating the production of round lenses therefrom;

FIG. 9 is an illustration of lenses which may be produced from the preform of FIG. 8 by transaxial cutting thereof;

DESCRIPTION OF THE PREFERRED EMBODIMENTS

Figure 10:
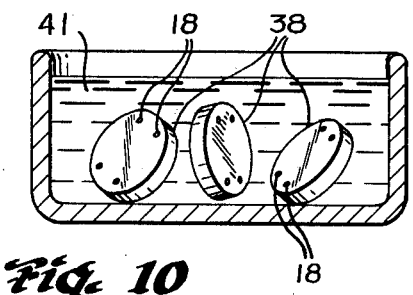
FIG. 10 is a view illustrating a leaching process used to form holes in the lenses according to the invention.

Referring more particularly to FIGS. 1 and 2 of the drawings, pseudophakos 10 comprises a lens 12 having a pair of posterior iris clips 14 for fixturing within the eye 16. This form of pseudophakos, which is shown for purposes of illustration only, is commonly referred to as an "iridocapsular lens" or "two-loop lens". Its fixation is in the iridocapsular cleft substantially as illustrated. Lens 12 is formed of a material which is biologically inert, i.e. not susceptible to being absorbed by body fluids and capable of being well tolerated by the human body when implanted. Exemplary base glasses are soda borosilicates and sodium titania silicates wherein all raw materials, particularly $SiO_2$ are selected to be types which are free of traces of radioactive substances. Desirable glasses are compositions which may be produced according to standard glass-making techniques with raw materials consisting of high purity silica, nitrates of sodium and barium, carbonates of sodium, strontium, calcium and manganese and oxides of titanium, zirconium, cerium, boron, zinc, iron and copper. It is, nevertheless, required for the sake of maintaining high purity that such glasses be made in glass makers platinum crucibles and with similarly non-contaminating stirrers. It is also highly desirable that the lens material have optical transmission properties simulating the optical absorption of the human crystalline lens and exemplary glass compositions of this type are set forth in co-pending application Ser. No. 615,276 which was filed on Sept. 22, 1975. Other ophthalmic lens glasses which are free from toxicity and radioactivity and are preferably of low density may, of course, be used.

Iris clips 14 which comprise loops of wire having their opposite ends secured to lens 10 are, for reasons of avoiding irritation and/or human body rejections, formed of a biologically inert material such as platinum, titanium, tantalum or an extruded polyamide such as nylon or one or more of other resins including methylmethacrylate or biologically neutral chemically pure polymethylmethacrylates or biologically inert polymeric materials.

Iris clips 14 and others to be described hereinafter will be referred to as being "wire" of "formed of wire". Accordingly, it should be understood that the term "wire" as used in this specification and its appended claims is intended to include strands, strips, rods or fibers of biologically inert material whether the material is metallic or plastic and whether one or both is used to make up a particular array of iris clips or other lens fastening components.

Iris clips such as 14 are conventionally fastened to lenses such as lens 10 by force-fitting into openings provided in the lenses. To this end, each lens 10 requires the provision of holes 18 (FIG. 3) of predetermined carefully controlled diametral dimension and relative juxtaposition according to the locations desired for anchoring the ends of iris clips 14.

In avoiding prior art problems of having to form such holes by spotting and drilling each lens and further having to contend with the previously mentioned problems of roughness, flaking, chipping and/or incipient cracking inherent in lens drilling operations, the following procedure for producing openings 18 in lenses such as lens 10 is contemplated:

A glass-casting mold 20 (FIGS. 5 and 6) having an elongated casting cavity 22 and perforated opposite end walls 24 is provided. Cavity 22 which may be of any desired cross-sectional configuration, preferably has a semi-circular base 24 of a radius of curvature equal to or greater than that desired of intraocular lenses to be produced according to the invention. With base 24 as a reference surface, openings 26 in end walls 23 are located in such predetermined relative juxtaposition as to represent the spaced positions desired of holes to be produced in lenses of diametral dimensions corresponding to the curvature of base 24. Wires 28 threaded through each of pair of corresponding openings in opposite walls 23 are drawn taught in cavity 22 and secured thereinplace, e.g. by knotted ends 30 or with suitable clamps, not shown. It should be understood that wires 28 (FIG. 5) may be formed of a single strand threaded back and forth through openings 23 and having its opposite ends secured against retraction after the extensions across cavity 20 are drawn taught.

Wires 28 are preferably formed of steel or other material which is capable of being attacked by acids to which ophthalmic glass is resistant and thereby subsequently selectively etched away after the glass is cast therearound as will be described in detail shortly. These wires 28 must, however, be sufficiently refractory to withstand glass melting temperatures.

A high chrome steel capable of being selectively etched with boiling concentrated sulfuric acid will produce desirable results. A useful composition comprises:

| Material | Weight Percent |
| --- | --- |
| iron (Fe) | 68.24 |
| copper (Cu) | 1.90 |
| aluminum (Al) | 6.30 |
| carbon (C) | 0.06 |
| chromium (Cr) | 23.5 |

Mold 20, may, for example, be formed of cast iron, graphite, alloys of copper, tin and aluminum or beryllium and nickel.

Mold 20, with wires 28 held taught therein is filled with a preselected molten ophthalmic lens glass which, following cooling in place produces preform 32. Opposite ends of wires 28 adjacent walls 23, are cut and preform 32 (FIG. 7) is removed for finishing into lenses. Mold 20 may, alternatively, be provided with removable end walls 23 to facilitate the removal of preform 32. Desirable glass compositions and methods of making same are set forth in the aforementioned co-pending patent application Ser. No. 615,276 filed Sept. 22, 1975.

The finishing of preform 32 would preferably include a first step of grinding away edges 34 (FIG. 7) to the extent of providing the preform with a completely circular cross-sectional configuration uniformly throughout its length as illustrated in FIG. 8. Transaxial cutting of the thus cylindrically shaped preform 32 along lines 36 will then produce lenses 38 (FIG. 9).

Sections 40 of wire 28 remaining in lenses 38 are next removed by immersion of the lenses 38 in a suitable etching solution 41 (FIG. 10), e.g. boiling concentrated sulfuric acid.

Having thus removed sections 40 or wire, holes such as are illustrated by reference numeral 18 in FIG. 3 result. These holes 18 are of diametral sizes corresponding to that of wires 28 and have wall surfaces of finished texture also corresponding to that initially provided upon wires 28. Finishing the surfaces and/or edges of lenses 38 to a desired final configuration of an intraocular lens, e.g. lens 10, may then be carried out.

It should be understood that the above-described sequence of steps including the grinding away of edges 34 of preform 32 (FIG. 7), transaxial cutting of the preform 32, etching away of sections of wires 40 and the finishing of lenses 38 may be altered as desired. For example, the transaxial cutting of preform 32 may be effected before removal of sharp edges 34 and the lenses 38 individually edge ground or finished to circular configurations. Alternatively, the final surface finishing and/or edging of lenses 38 may be effected prior to etching of sections 40 of wire therefrom.

Referring to FIGS. 11-14, there is illustrated another technique for producing lenses according to the invention. This involves the formation of a slab-like preform 42 (FIG. 12) from which lens segments 44 (FIG. 13) may be cut and subsequently ground to the desired finished lens shapes of which lens 46 (FIG. 14) is exemplary.

The casting of slab 42 may be accomplished with fixture 48 (FIG. 11) having spaced perforated plates 50 and 52 supported by corners 54. The space between plates 50 and 52 is preferably closed along three sides of fixture 48 to form a casting cavity 56 into which a glass used to form the slab 42 may be poured.

Preforations 58 and 60 in plates 50 and 52 respectively, are preferably identically geometrically patterned and disposed in directly oppositely spaced relationships. They are further arranged in groups each corresponding in number and relative juxtaposition to the number and spaced positions desired of holes to be formed in lenses such as lens 46.

Figure 11:
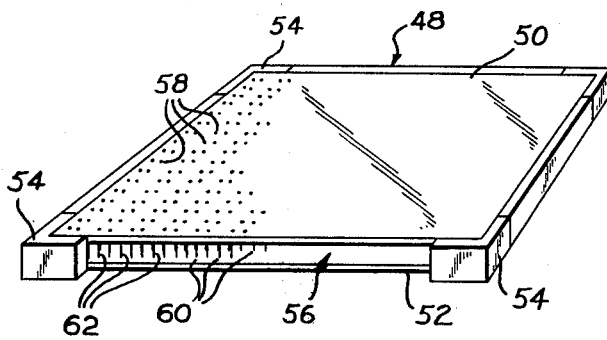
FIG. 11 is a diagrammatic illustration of another form of apparatus useful in the manufacture of multiple lens preforms.
Figure 12:
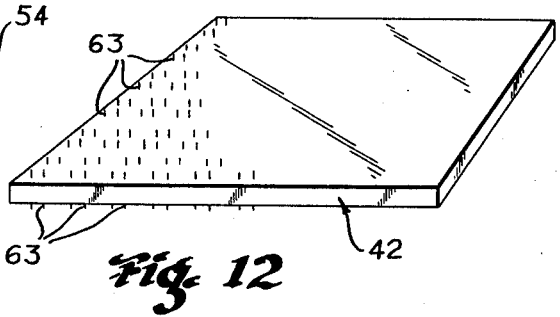
FIG. 12 is an illustration, in perspective, of the type of preform producable with the apparatus of FIG. 11.
Figure 13:
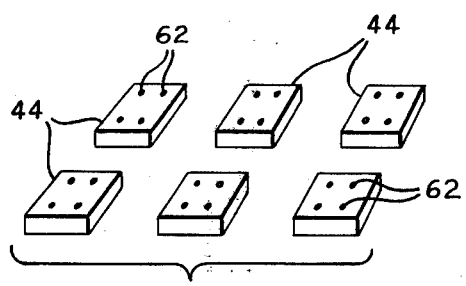
FIG. 13 is an illustration of a multiplicity of partially finished lenses of types which may be cut from the preform of FIG. 12.
Figure 14:
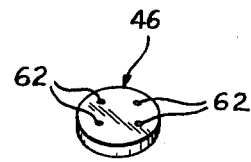
FIG. 14 illustrates the result of further finishing of the lenses of FIG. 13.

Wires 62 are extended across cavity 56 from each of oppositely disposed perforations 58 and 60 substantially as illustrated in FIG. 11. Wires 60 may each extend individually through plates 50, 52 and across cavity 56 or comprise the extensions of one or more relatively long lengths of wire threaded back and forth through and across plates 50 and 52. In the latter case, portions of wire interconnecting perforations 58 across outer surfaces of plates 50 and 52 would require removal to permit separation of plates 50 and 52 after forming a glass casting within cavity 56. This may be accomplished prior to or following the casting step.

With all wires 62 in place and all other components of fixture 48 held intact, the selected open end of cavity 56 would preferably be directed upwardly and a preselected molten glass poured thereinto until filled. After cooling of the glass thereinplace, disassembly of fixture 48 and lifting of plates 50 and 52 away from a resulting slab 42 will render the slab adaptable to cutting into lens rectangular segments 44. Circular segments may be produced by trepanning. It is preferable to remove all exposed opposite ends 63 of wires 62 prior to cutting of the slab. These ends 63 may, however, be removed later, if desired.

As mentioned hereinabove, lens segments 44 may then be edge ground and surface finished to shapes and sizes desired of finished lenses. Wires 62 remaining internally of the finished lenses are etched away in the manner shown and described relative to lenses 38 (FIG. 18). In this case, it should be understood that the etching operation may be preformed prior to surface and edge finishing of lenses 46 if desired. In fact, etching may be performed subsequent to the cutting of slab 42 into segments 44 or the slab 42 itself may be subjected to the etching operation to remove wires 62 before performance of cutting operations used to produce lens segments 44. The aforementioned ends 63 of wires 62 may be etched away rather than cut, if desired.

In all of the aforementioned examples of practice of the present invention, holes are produced in the lenses which are of sizes and inner wall surface textures corresponding to the size and outer surface finish respectively of wires 62 or 28. Positions of these holes in respective lenses correspond to the predetermined relative alignment of the wires in their respective glass casting molds or fixtures.

Completion of a pseudophakos such as 10 (FIG. 1) having a lens 12 with openings 18 formed according to the invention includes the fitting of opposite ends of wire iris clips 14 into the holes. By control of relative hole and wire sizes, an interference fit locking the two together can be accomplished.

Figure 15:
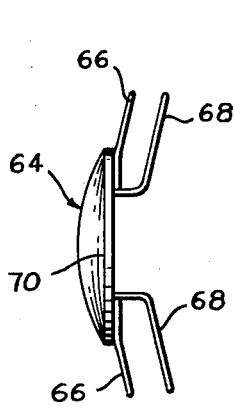
FIGS. 15, 16 and 17 illustrate examples of various modified forms of pseudophakoi to which the method of the present invention is applicable.
Figure 16:
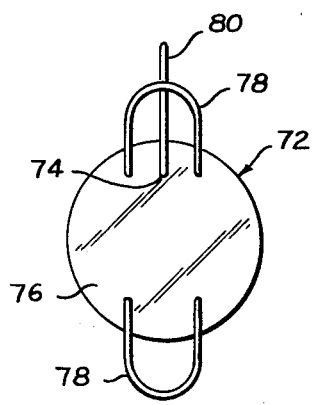
Figure 17:
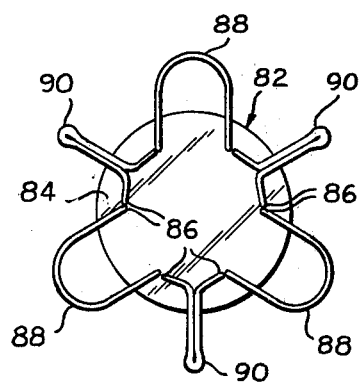

Alternative forms of pseudophakoi to which the present invention is similarly applicable are shown in FIGS. 15-17. In the arrangement of pseudophakos 64 of FIG. 15, anterior iris clips 66 are provided in addition to posterior iris clips 68. This is typical of the well-known type of pseudophakos referred to in the art as a "two-loop lens" and it is implanted with the iris extended between anterior and posterior clips 66 and 68. This automatically centers behind lens 70.

The embodiment of pseudophakos 72 (FIG. 16) is generally similar to pseudophakos 10 of FIGS. 1-3. In addition to the structure of lens 76 and the dual posterior iris clips 78, however, there is provided a fifth opening 74 produced according to the invention and into which one end of a wire clasp 80 is fastened. In use, pseudophakos 72 is implanted with clips 78 in the iridocapsular cleft and wire 80 is extended over the iris, through an iridectomy and around its adjacent iris clip 78. This minimizes luxation of the pseudophakos.

Pseudophakos 82 of FIG. 17 has lens 84 provided with openings 86 into which wires are extended. In the particular configuration illustrated, three posterior iris clips 88 are provided and three anterior wire struts 90 are formed.

Those skilled in the art will readily appreciate that there are various other modifications and adaptations of the precise forms of the invention here shown which may be made to suit particular requirements. For example, in instances where the characteristics of particular combinations of lens-casting materials and wire may, after casting and cooling, produce sufficient loosening of the wires to permit their removal without etching, e.g. by pulling, the method step of removal of the wires may not necessarily require the above-described operation of etching. Accordingly, the precise forms of the invention herein shown and described are not to be interpreted as restrictive of the invention beyond that neccessitated by the following claims.

We claim:

1. The method of making a lens for a pseudophakos having spaced apart holes of preselected diametral dimension adjacent its edge comprising the steps of:

aligning and fixedly supporting a plurality of wires in spaced juxtaposition, the spacings between said wires corresponding to spacings between said holes to be produced in said lens and said wires being of diametral dimension corresponding to the diametral size preselected for said holes;

casting a molten ophthalmic lens glass over and around said plurality of wires;

allowing said molten glass to cool in place about said wires to produce a rigid preform of said lens;

removing said wires to produce holes in their place; and at one stage of the process following said step of allowing said molten glass to cool, cutting, grinding and polishing at least a portion of said preform to the final size and configuration desired of opposite optical surfaces, center thickness and edge configuration of the finished pseudophakic lens.

2. The method according to claim 1 wherein said wires are selectively etchable and said removal thereof is effected by subjecting the cast lens material to a wire etching medium.

3. The method according to claim 2 wherein said metal is a high chrome steel and said etching medium is sulfuric acid.

4. The method according to claim 1 wherein said wires are extended across a casting cavity of a mold and said lens-forming material is cast in said cavity.

5. The method according to claim 1 wherein said lens is cast as a part of a multiple lens preform and subsequently cut away therefrom, said wires being extended through said multiple lens preform in said rearranged spaced relationships of juxtaposition.

6. The method according to claim 5 wherein said preform is of a relatively long and thin configuration from which said lens is cut transaxially and said wires extend longitudinally through said preform.

7. The method according to claim 6 wherein said preform is formed to a circular cross-sectional configuration prior to said transaxial cutting of said lens therefrom and, following said cutting, said lens is ground and polished to a desired finished configuration.

8. The method according to claim 5 wherein said preform is in the configuration of a slab having a thickness at least equal to that desired of said lens and from which said lens is cut, said wires being extended through said slab in the direction of its thickness and said lens is cut around said wires.

* * * * *